United States Patent
Kullik et al.

(10) Patent No.: US 11,529,052 B2
(45) Date of Patent: Dec. 20, 2022

(54) DEVICE FOR CONTROLLING AN OPERATING STATE OF AT LEAST ONE MEDICAL DEVICE IN A MEDICAL DATA NETWORK AS WELL AS MEDICAL DEVICE FOR A MEDICAL DATA NETWORK

(71) Applicant: Drägerwerk AG & Co. KGaA, Lübeck (DE)

(72) Inventors: Götz Kullik, Lübeck (DE); Stefan Schlichting, Lübeck (DE); Volker Mildner, Lübeck (DE); Joshua Abell, Beverly, MA (US)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 1099 days.

(21) Appl. No.: 15/850,559

(22) Filed: Dec. 21, 2017

(65) Prior Publication Data
US 2018/0177398 A1    Jun. 28, 2018

(51) Int. Cl.
| | |
|---|---|
| G06Q 40/08 | (2012.01) |
| A61B 5/00 | (2006.01) |
| G16H 40/60 | (2018.01) |
| G16H 40/67 | (2018.01) |
| A61M 5/172 | (2006.01) |
| G16H 20/10 | (2018.01) |

(52) U.S. Cl.
CPC ........... *A61B 5/0022* (2013.01); *G16H 40/60* (2018.01); *G16H 40/67* (2018.01); *A61B 5/0004* (2013.01); *A61M 5/1723* (2013.01); *G16H 20/10* (2018.01)

(58) Field of Classification Search
CPC .......... A61N 1/08; A61M 5/168; H04W 4/08; A63F 13/428; A61H 9/0007

USPC ................. 607/60; 604/66; 455/519; 482/8; 128/204.23
See application file for complete search history.

(56) References Cited

U.S. PATENT DOCUMENTS

| | | | |
|---|---|---|---|
| 6,571,128 B2 * | 5/2003 | Lebel | G16H 40/40 607/60 |
| 2007/0168222 A1 | 7/2007 | Hoyme et al. | |
| 2011/0009813 A1 * | 1/2011 | Rankers | A61B 5/15087 604/66 |
| 2012/0163663 A1 | 6/2012 | Masoud et al. | |

(Continued)

FOREIGN PATENT DOCUMENTS

| | | |
|---|---|---|
| WO | 2016/179389 A1 | 11/2016 |

OTHER PUBLICATIONS

Google patents, Mar. 27, 2020 (Year: 2020).*
Google patents search, Jun. 25, 2021 (Year: 2021).*
ip.com search, Jan. 26, 2022 (Year: 2022).*

*Primary Examiner* — Dilek B Cobanoglu
(74) *Attorney, Agent, or Firm* — McGlew and Tuttle, P.C.

(57) ABSTRACT

A device, such as a data network device for a medical data network, controls an operating state of a second medical device in such a way that by sending a request message, the second medical device is prompted to change over into the operating state of the combined therapy and hence into an operating state in which its actuator is controlled as a function of an information signal of the first medical device. The information signal is based on physiological measured values. As a result, a clinician does not have to configure the second medical device himself/herself directly on site at the medical device by inputting an input signal, but this can be carried out by the device.

20 Claims, 10 Drawing Sheets

(56) References Cited

U.S. PATENT DOCUMENTS

| | | | |
|---|---|---|---|
| 2014/0081654 A1* | 3/2014 | Bechtel | G16H 70/00 |
| | | | 705/2 |
| 2014/0150791 A1* | 6/2014 | Birnkrant | A61H 9/0007 |
| | | | 128/204.23 |
| 2014/0164519 A1 | 6/2014 | Shah | |
| 2014/0180711 A1* | 6/2014 | Kamen | G16H 20/10 |
| | | | 705/2 |
| 2014/0222450 A1 | 8/2014 | Gray et al. | |
| 2015/0094111 A1* | 4/2015 | Kim | H04W 4/08 |
| | | | 455/519 |
| 2015/0355789 A1 | 12/2015 | O'Mahony et al. | |
| 2016/0096072 A1* | 4/2016 | Rahman | A63F 13/428 |
| | | | 482/8 |
| 2018/0015218 A1* | 1/2018 | Welsch | A61M 5/172 |

* cited by examiner

FIG. 6a
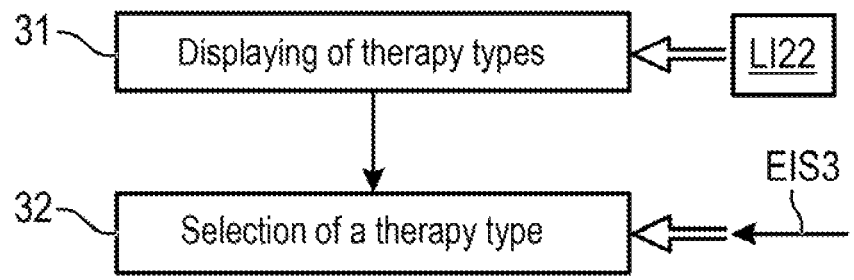
FIG. 6b
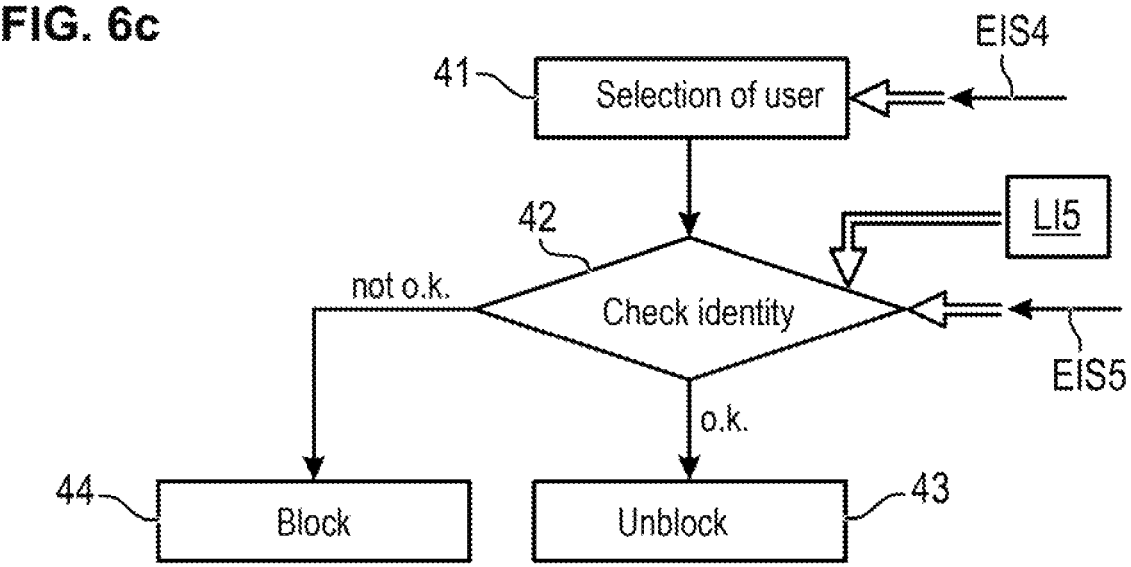
FIG. 6c

| TTX | TB | VW2 | TB | VW21 | ... |
|---|---|---|---|---|---|
| ⋮ | ⋮ | ⋮ | ⋮ | ⋮ | |

| U1 | UID1 |
|---|---|
| ⋮ | ⋮ |

| IDZ | ABO | ... |
|---|---|---|

US 11,529,052 B2

DEVICE FOR CONTROLLING AN OPERATING STATE OF AT LEAST ONE MEDICAL DEVICE IN A MEDICAL DATA NETWORK AS WELL AS MEDICAL DEVICE FOR A MEDICAL DATA NETWORK

CROSS REFERENCE TO RELATED APPLICATIONS

This application claims the benefit of priority under 35 U.S.C. § 119 of German Application 10 2016 015 685.6, filed Dec. 22, 2016, the entire contents of which are incorporated herein by reference.

FIELD OF THE INVENTION

The present invention pertains to a device for controlling an operating state of at least one medical device for a combined therapy of a patient by the interaction of at least two medical devices in a medical data network.

BACKGROUND OF THE INVENTION

It is sometimes desirable in a medical setting for a plurality of medical devices to interact in order to make possible a healing process or a therapy of a patient. A first medical device may detect here via a sensor physiological measured values related to a physiological parameter of a patient, which can then be analyzed in order to actuate an actuator of a second medical device as a function of the physiological parameter. Such an actuator may be, for example, a gas feed unit of a ventilator (also known as a respirator) as an example of a second medical device. A first medical device is, for example, a so-called physiological patient monitor, which detects voltage potentials as measured values on respiratory muscles, e.g., on the basis of EMG electrodes or electromyography electrodes.

The first medical device may determine, for example, measured values filtered or processed from physiological measured values and then make these available as an information signal to the second medical device via a data network, so that the second medical device uses the values indicated in the information signal for selecting an operating parameter value of the actuator. Such an operating parameter of an actuator may be, for example, a predefined pressure value for a pressure-controlled ventilation by means of the gas feed unit.

SUMMARY OF THE INVENTION

An object arising for a clinician is consequently that a plurality of medical devices must be configured correspondingly in order for these medical devices to act together and jointly in order to bring about an adequate influence on the patient.

Due to the fact that a combined method of treatment or combined therapy of a patient shall be brought about in the medical device data set for the combined therapy, the medical devices involved must be configured correspondingly, so that the desired interaction of the medical devices is indeed carried out. In other words, the plurality of necessary medical devices must optionally be configured correspondingly each for itself, so that the interaction or the combined therapy will be carried out correctly.

Such an interaction of medical devices represents a critical influence on the patient, so that a high degree of clinical liability and possibly legal risks are associated with the activation of the mode of operation of the combined therapy or of the interaction for a clinician.

A method for configuring the medical devices should therefore be safe, trustworthy and also reliable from the viewpoint of a clinician. There is therefore a need for providing an automated method for an automatic configuration of medical devices for one medical device or for a plurality of medical devices to be used in combined therapy, so that a clinician does not have to perform a separate, individual configuration on site on all of the individual medical devices.

If a clinician had to configure every individual of the medical devices in itself, it would eventually be possible that an uncertain interaction of the medical devices could develop due to the fact that even though a first of the medical devices would already be configured for the combined therapy, another medical device would not yet be configured correctly for an interim time period, so that all the medical devices fail to interact correctly for the combined therapy and an undesired influence on the patient would be possible.

The object according to the present invention is accomplished by a device for controlling an operating state of at least one medical device for a combined therapy of a patient by the interaction of at least two medical devices in a medical data network according to patent as well as by a medical device for a medical data network.

Consequently, a solution is provided in which a device, preferably a data network device for a medical data network, controls an operating state of a second medical device in such a manner that by sending a request message, the second medical device is prompted to change over into the operating state of the combined therapy and thus into an operating state in which its actuator is controlled as a function of an information signal of the first medical device, which information signal is based on physiological measured values. As a result, a clinician does not have to configure the second medical device himself/herself directly on site at the medical device itself by inputting an input signal, but this can be carried out by the device according to the present invention.

The solution according to the present invention proposes a device which is configured to control an operating state of at least one medical device for a combined therapy of a patient by the interaction of at least two medical devices in a medical data network, wherein a first medical device is configured to detect physiological measured values of a patient in an operating state of a combined therapy and to generate an information signal on the basis of the physiological measured values as well as to provide the information signal via the data network. A second medical device has an actuator for physiologically influencing the patient and is configured to select at least one operating parameter of the actuator in the operating state of the combined therapy as a function of the information signal of the first medical device, which information signal is received via the data network. The device has a data network interface, an input unit for inputs of a user, an optical display unit for outputting information for the user, as well as a control unit. The control unit is configured to determine a current joint assignment of the first and second medical devices to a group in the data network on the basis of data messages received via the data network interface as well as to display the current joint assignment of the first and second medical devices to the group via the display unit for the user in case of a positive result of the determination, and, upon receipt of a confirmation signal from the input unit, to send to the second medical device a request message, which indicates a request to activate the operating state of the combined therapy in the second medical device.

As was already mentioned above, the device according to the present invention consequently makes it possible to carry out a configuration of the operating state for the combined therapy at least for the second medical device in an automated manner. Due to the control unit of the device determining the current joint assignment of the medical devices to a common group on the basis of the received data messages, it is not necessary for the clinician to define or form the group of the cooperating medical devices from all the medical devices present in the medical data network. This is advantageously carried out by the assignment of the medical devices to a common group being able to be determined on the basis of data messages, which are received via the data network interface of the device and which may originate from the medical devices. The group is preferably predefined by a memory unit of the device providing a data element of a group identification, so that the control unit then determines a current joint assignment of the first and second medical devices to the common, predefined group in the data network on the basis of the data element.

As a result, the clinician is consequently relieved of the burden of having to take into consideration a plurality of medical devices of the medical data network in order to determine which medical devices shall interact for the combined therapy. A total number of different medical devices from a medical data network could be very large and could be very confusing for the clinician in a display mode of a display unit of a data network device, so that a selection of medical devices to be performed by the clinician from the total number of medical devices present in the medical network could represent a laborious procedure.

Due to the fact that in case of a positive result of the determination of the current joint assignment of the medical devices to the group of medical devices, this current joint assignment of the medical devices is displayed to the user via the display unit, the user is informed of the medical devices that are taken into consideration or proposed by the device according to the present invention for the combined therapy. As a result, the clinician consequently has the possibility of checking himself/herself once again the medical devices of the corresponding group, which are assigned to the combined therapy in an automated manner, by means of the display on the display unit.

Due to the fact that the sending of the request message to the second medical device with the request to activate the operating state of the combined therapy takes place only after a confirmation signal has been received from the input unit, the user has control over whether the second medical device will, indeed, change over into the operating state of interaction with other devices or to the operating state of combined therapy. Further, the clinician is hereby relieved of the burden of having to perform detailed or separate configuration on the second medical device.

The current joint assignment of the first medical device and of the second medical devices to the group may preferably be displayed in the form that, for example, identification data of the first and second medical devices are displayed in a list and that, further, an image element is displayed, which displays the positive result of the determination. Such an image element may be, for example, a green checkmark.

The displaying is preferably carried out by identification data of the first and second medical devices with respective network identification being offered in a list and by corresponding display information, which indicates a respective medical device type of the first and second medical devices, being further offered additionally for each medical device.

The request message is preferably a first request message, and the control unit is further configured to send a second request message, which indicates a request to activate the operating state of the combined therapy in the first medical device, to activate the first medical device in the presence of the confirmation signal.

This embodiment of the device according to the present invention is advantageous because it is possible to control not only the second medical device, which has the actuator to be controlled, in order to carry out the interaction during the combined therapy, but also whether the first medical device is indeed providing the information signal, which is generated on the basis of the physiological measured values, for the second medical device via the data network. If the first medical device would provide the information signal in any desired operating state, this could, for example, represent an unnecessary burden of the medical data network concerning the amount of data generated in the network. Further, an undesired sending of the information signal, which could contain physiological measured values of the patient, could represent a security risk in the data network concerning data security. These problems are avoided, because the time beginning from which the first medical device does indeed provide the information signal, which is generated on the basis of the physiological measured values, via the data network or in the data network can be controlled by the device according to the present invention by means of the request message to the first medical device.

The device according to the present invention is preferably configured such that in case of a positive determination result, the control unit clears the input unit for a potential input of the confirmation signal. In this case, the meaning of clearing means is that the input unit is configured by a control of the control unit such that the input of the confirmation signal into the input unit is possible after the clearing, but not before the clearing. An alternative embodiment of clearing is that confirmation signals can already be inputted into the input unit by the input unit before the clearing, and these confirmation signals are then made available to the control unit by the input unit, but the control unit takes the confirmation of the input unit into consideration only when the clearing has taken place.

The device according to the present invention is preferably configured such that it has a memory unit, which is configured to provide a medical device data set, which indicates a corresponding set of medical device types necessary for the type of combined therapy for at least one type of combined therapy. The control unit then compares the set of necessary types of medical devices with the medical devices or with the first and second medical devices, for which the current joint assignment to a common group was determined, in order to then clear the input unit for the potential input of the confirmation signal only when a corresponding medical device is currently also assigned to the common group for each necessary medical device type from the corresponding medical device data set. Care is thus taken to ensure that the request message can be sent to the second medical device and preferably the request message can be sent to the first medical device based on the input of the confirmation signal for the configuration of the second medical device and preferably of the first medical device only when all the necessary medical device types are also indeed assigned to the current common group for the desired combined therapy.

The device according to the present invention preferably has, furthermore, a memory unit. The memory unit is configured to provide a medical device data set, which indicates for a combined therapy type a corresponding set of medical device types necessary for the combined therapy type. The control unit is further configured to determine on the basis of the data set and the received data messages whether a corresponding medical device is currently assigned to the common group from the set for each indicated medical device type and in case no corresponding medical device is currently assigned to the group for at least one of the indicated medical device types, to display to the user via the display unit the particular necessary, indicated medical device types to which no corresponding medical device is currently assigned in the common group.

This embodiment of the device according to the present invention is advantageous because the device checks in an automated manner whether a corresponding medical device is indeed assigned for each necessary medical device type from the corresponding set, and this is determined on the basis of the data set and the received data messages in an automated manner, so that a user is ultimately informed about the medical device type for which a corresponding medical device is still missing in the group for the combined therapy. The user is consequently supported in an automated manner to determine whether the combined therapy can already be carried out or whether a certain medical device of a certain medical device type is still missing.

The displaying of the medical device types for which no corresponding medical device is currently still assigned to the group or the predefined group can be carried out by displaying in a list the corresponding one medical device type or the plurality of corresponding medical device types as list elements.

The device is preferably configured such that the control unit is further configured to prevent the sending of the request message as a function of an input signal of the input unit.

This embodiment of the device according to the present invention is advantageous because it is possible thereby for a user to terminate the process of initiating the combined therapy by configuring the operating states on the medical device and preferably on the first medical device by an input into the input unit.

The device is preferably configured such that the control unit is configured to identify on the basis of the medical device data set and the received data messages at least one additional medical device from the data network, which medical device is potentially considered for displaying the at least one additional medical device for the user via the display unit.

This embodiment of the device according to the present invention is advantageous because the device or the control unit independently identifies, in an automated manner, a medical device that is considered for the combined therapy type even though it is not currently assigned to the common group of medical devices.

The control unit is preferably configured to determine information related to the availability of the at least one additional medical device on the basis of the received data messages and to display the information to the user via the display unit.

Here, availability may preferably be information related to the location of the medical device. As an alternative, the availability may preferably be a switched-on state or switched-off state of the additional medical device.

This embodiment of the device according to the present invention is advantageous because the user obtains information in an automated manner about whether the at least one additional medical device, which is displayed to him, has an availability status that is of interest to him.

The control unit is preferably configured to perform an assignment of the at least one additional medical device to the common group as a function of an input signal of the input unit.

This embodiment of the device according to the present invention is advantageous because it is thus made possible for the user to assign an additional medical device displayed in the display unit to the group in an automated manner.

The control unit is further preferably configured to send a signal to the additional medical device via the data interface, wherein the signal may be a data message, which indicates an assignment to the common group. The additional medical device is then consequently informed hereby about the desired assignment to the common group.

The control unit is preferably configured to identity on the basis of the received data messages a plurality of additional medical devices from the data network, which are not yet assigned to the common group but are potentially considered for the combined therapy type. A plurality of additional medical devices are displayed via the display unit in an order that depends on a predefined criterion.

This embodiment of the device according to the present invention is advantageous because if a plurality of additional medical devices are potentially considered for being assigned to the common group, the displaying of these medical devices depends on a predefined or predefinable criterion. The user may preferably select the predefined or predefinable criterion himself/herself by an input into the input unit. As a result, the device according to the present invention can then consequently be configured by the user with respect to the criterion to be applied.

Such a criterion may be, for example, a quality level of the medical devices that are considered. Consequently, if a user would like to select one medical device from a plurality of additional medical devices that are considered for a certain medical device type, he is possibly interested in selecting each additional medical device that has such a quality level, which is higher than the quality levels of the other, additional medical devices.

The device according to the present invention is preferably configured to provide a medical device data set, which indicates respective, corresponding sets of a plurality of necessary medical device types for respective combined therapy types. The control unit is then further configured to display to the user the respective combined therapy types as well as to determine a selection of a certain combined therapy type as a function of an input by the user via the input unit.

This embodiment of the device according to the present invention is advantageous because the user can thus select from a plurality of possible combined therapy types. A therapy type or a plurality of therapy types are preferably selected and then proposed from the respective combined therapy types of the medical device data set as a function of medical devices or medical device types detected on the basis of the data messages. This special embodiment is advantageous because only such combined therapy types are proposed as a result that correspond to the one already detected medical device or medical device type or to a plurality of already detected medical devices or medical device types. Consequently, this makes possible a meaningful preselection of a combined therapy type from the medical device data set as a function of already detected medical devices or medical device types.

A selection of combined therapy types from the medical device data set is preferably performed on the basis of data information that was received via the data interface at the device. As a result, it will consequently become possible for an information or diagnostic system in the sense of a central IT system of a clinical setting to predefine for the device the combined therapy types that are considered for a certain group or for a certain patient by means of a data message or a plurality of data messages.

The control unit is preferably configured to provide an identification data set, which indicates an identity or a plurality of identities of respective authorized users. Further, the control unit is configured to receive an input signal, which indicates an identity of the user, via the input unit or an additional input unit, and further to control the input unit such that the control unit makes the possibility of an input into the input unit for generating the confirmation signal dependent on a comparison of the identification data set and the input signal, which indicates the identity of the user.

This embodiment of the device according to the present invention is advantageous because the trustworthiness of the device as a central configuration element for different medical devices for achieving a combined therapy is consequently increased for a user. As a result, a user may come to believe that the device according to the present invention is especially secure because only authorized users may indeed start the combined therapy.

The control device is preferably configured to make possible the input for generating the confirmation signal in case of a positive result of the comparison for a predefined duration only.

This embodiment of the device according to the present invention is advantageous because a user can thus see that after unblocking the system or the input unit, an input for generating the confirmation signal and hence for configuring medical devices is not possible for a duration but is ended after a predefined duration. As a result, the user will consequently see that after unblocking the input unit, a configuration of medical devices for the combined therapy is only possible during the predefined duration and that the device according to the present invention could not be misused, e.g., by another, unauthorized user being able to make inputs into the input unit for configuring the medical devices for the purpose of the combined therapy at a markedly later time.

The request message preferably indicates at least one predefined value relative to at least one operating parameter of the actuator.

This embodiment of the device according to the present invention is advantageous because it is made possible hereby for the second medical device to operate its actuator relative to the operating parameter in a desired manner with the use of the predefined value during an initial phase of the combined therapy. Thus, an initial actuation can consequently be selected for the actuator by the device according to the present invention during the initial phase of the combined therapy.

The medical device data set preferably indicates for at least one combined therapy type at least one predefined condition, which must be met during a course of a combined therapy type, and the control unit is further configured to indicate the predefined condition in the request message.

This embodiment of the device according to the present invention is advantageous because the device can predefine in the request message the condition that must be met by a medical device during the operating state of the combined therapy. It can be guaranteed hereby that a predefined condition can be monitored by the medical device, which receives the request message, in order thus to carry out the combined therapy especially safely.

The control unit is preferably configured to check whether the predefined condition was met on the basis of data messages received via the data interface and to send at least one request message to the first and/or second medical device if the result of the checking was negative, this request message indicating a request for terminating the operating state of the combined therapy.

This embodiment of the device according to the present invention is advantageous because the device can check itself on the basis of the messages whether the predefined condition is indeed met, and by using the sending of the request message, which indicates a request to terminate the combined therapy, it has the possibility of configuring the first and/or second medical device such that the combined therapy is not carried out any longer.

Further, a medical device for a medical data network is proposed, which has an actuator for physiologically influencing a patient, a data network interface as well as a control unit for controlling the actuator. The control unit is further configured to select at least one operating parameter of the actuator as a function of at least one information signal received from another medical device via the data network interface in an operating state of a combined therapy and to activate the operating state of the combined therapy in the medical device upon receipt of a request message.

The medical device according to the present invention is advantageous because it makes it possible for it to change over, by receiving the request message via the data network interface, into an operating state in which it selects at least one operating parameter of its actuator as a function of an information signal, which is received from another medical device via the data network interface.

As an alternative, the information signal may be called an information data signal or information data message.

The control unit is preferably configured to end the operating state of the combined therapy in the medical device upon receipt of an additional request message.

This embodiment of the medical device according to the present invention is advantageous because not only an activation of the operating state of the combined therapy, but also the termination thereof or the end thereof can be configured by sending a request message to the medical device.

The control unit is preferably configured to receive via the data network interface a request message, which indicates at least one predefined condition, which must be met during the operating state of the combined therapy. Based on data messages received via the data interface and/or own sensor signals, it must be possible to check whether the predefined condition is met and to end the operating state of the combined therapy if the result of the checking is negative.

This embodiment of the medical device according to the present invention is advantageous because the medical device can be configured from the outside in the respect that it takes into consideration such a predefined condition for controlling the termination of the state of the combined therapy, which condition can be predefined for the medical device via a request message via the data network interface. In particular, the sensor signal of the medical device proper can be used hereby to check whether a predefined condition is met and the operating state of the combined therapy can then be ended if necessary.

The control unit is preferably configured to send at least one request message to at least one other network device of the data network if the result of the checking is negative, this request message indicating a request for ending the combined therapy.

This embodiment is advantageous because by sending the request message, which indicates a request to end the combined therapy, the medical device is able hereby to inform other medical devices or a central data network unit that the combined therapy shall be terminated.

The present invention will be explained in more detail below based on the figures on the basis of special embodiments without limitation of the general inventive concept. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 6a is a schematic view showing a medical device data set according to a preferred embodiment;

FIG. 6b is a flow chart showing partial steps of a partial method, which can be carried out on or by the control unit of the device according to the present invention;

FIG. 6c is a flow chart showing partial steps of a partial method, which can be carried out on or by the control unit of the device according to the present invention;

DESCRIPTION OF THE PREFERRED EMBODIMENTS

Figure 1:
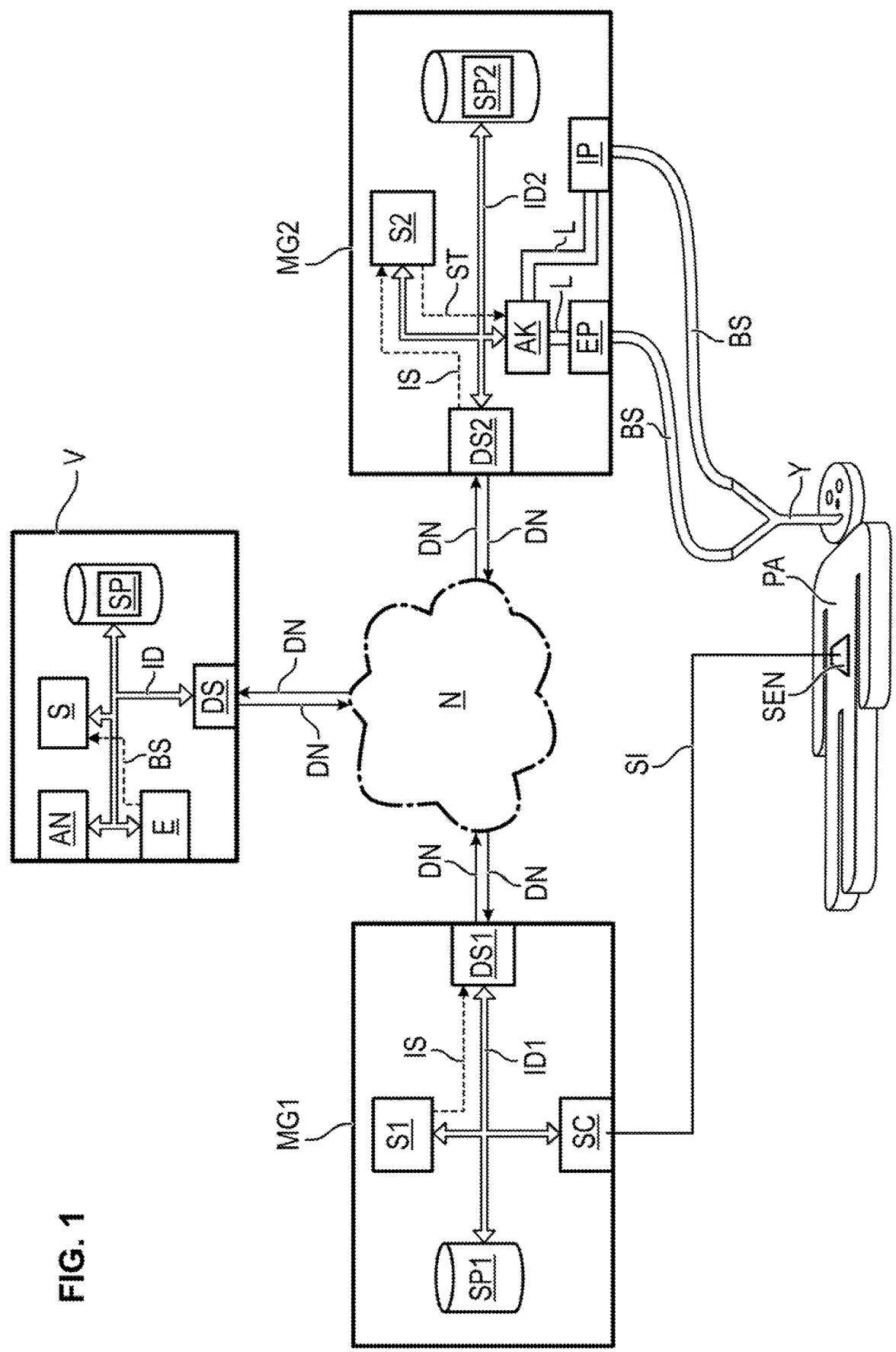
FIG. 1 is a schematic view showing different devices of a medical data network.

Referring to the drawings, FIG. 1 shows a device V according to the present invention, which is configured to control an operating state of at least one medical device MG2.

The device V has a data network interface DS for exchanging data messages DN via a medical data network N.

The device V further has a control unit S as well as an input unit E for inputting inputs of a user. The device V further has an optical display unit AN for outputting information to the user in optical form.

The input unit E and the display unit AN may preferably be in the form of an individual unit for inputting inputs or input signals and for displaying optical display signals. In such a case, such a combined unit comprising an input unit E and a display unit AN is, for example, a touchscreen.

A separate configuration of the display unit AN is, for example, a display for outputting information in the optical form.

A preferred embodiment of the input unit E is, for example, an input device in the form of buttons, a keyboard, a computer mouse or other usual input devices for data processing devices.

The memory unit SP, the control unit S, the data network interface DS, the input unit E as well as the display unit AN are preferably connected to one another via an internal data bus system ID.

FIG. 1 further shows a first medical device MG1, which has a memory unit SP1, a control unit DS1, a data network interface DS1 as well as a sensor interface SC.

The individual units are preferably connected to one another via an internal data bus ID1.

Via the sensor interface SC, the medical device MG1 detects a sensor signal SI of a sensor SEN. Such a sensor SEN may be positioned or arranged at or in a patient PA in order to detect physiological measured values of the patient PA via the sensor signal SI.

FIG. 1 further shows a second medical device MG2, which may be, for example, a ventilator. In case of a ventilator, the medical device MG2 preferably has an inhalation port IP as well as an exhalation port EP, via which parts of a ventilation tube BS lead to a Y-piece YS, via which the patient PA is ventilated. An actuator AK of the second medical device MG2 may be a gas feed unit for delivering breathing gas.

The second medical device MG2 consequently has an actuator for physiologically directly or indirectly influencing the patient PA.

The medical device MG2 further has a memory unit SP2, a control unit S2 as well as a data network interface DS2.

The actuator AK, the memory unit SP2, the control unit S2 as well as the data network interface DS2 are preferably connected to one another via an internal data bus ID2.

The control unit S2 is configured to control one or more operating parameters of the actuator AK via a control signal ST and thus to control and/or to regulate the actuator AK.

The medical device MG1 derives physiological measured values from the detected sensor signal SI. In a first preferred embodiment, the control unit S1 of the medical device MG1 generates an information signal IS, which indicates the detected physiological measured values or physiological measured values derived or processed therefrom. By means of one or more data messages DN, the control unit S1 of the medical device MG1 consequently provides physiological measured values for the second medical device MG2 via the data network N.

It may consequently be stated that the medical device MG1 generates the information signal IS on the basis of the physiological measured values.

In an alternative embodiment, the control unit S1 of the medical device MG1 detects physiological measured values of the patient PA and derives from this a predefined value for an operating parameter of the actuator AK of the second medical device MG2. This predefined value is then indicated by the information signal IS. The information signal IS is received at the medical device MG2 via the data network interface DS2 in the form of one or more data messages DN and then provided to the control unit S2. The control unit S2 selects at least one operating parameter of the actuator AK as a function of the information signal IS received via the data network.

The information signal IS preferably indicates physiological measured values, so that the control unit S2 itself selects a value for an operating parameter of the actuator AK on the basis of the physiological measured values and correspondingly actuates the actuator AK via the control signal ST.

The control unit S2 preferably uses a predefined value from the information signal IS in order to then select an operating parameter of the actuator AK by taking the predefined value into consideration and to correspondingly actuate the actuator AK via the control signal ST.

As was described above, the medical device MG2 may preferably be a ventilator, in which case the actuator AK is a gas feed unit.

As an alternative, the medical device MG2 may be an anesthesia device, in which the actuator AK may then be, for example, a dispensing unit for an anesthetic.

As an alternative, the medical device MG2 may be a syringe pump, wherein the actuator AK may be a liquid feed unit for feeding liquid drug to the patient PA.

In case the medical device MG2 is a ventilator, the operating parameter may preferably be a target pressure value for the gas feed unit. In case the medical device MG2 is an anesthesia device, the operating parameter may preferably be a gas concentration of an anesthetic. In case the medical device MG2 is a syringe pump, the operating parameter may preferably be a flow rate per unit of time for the liquid feed unit.

Figure 3:
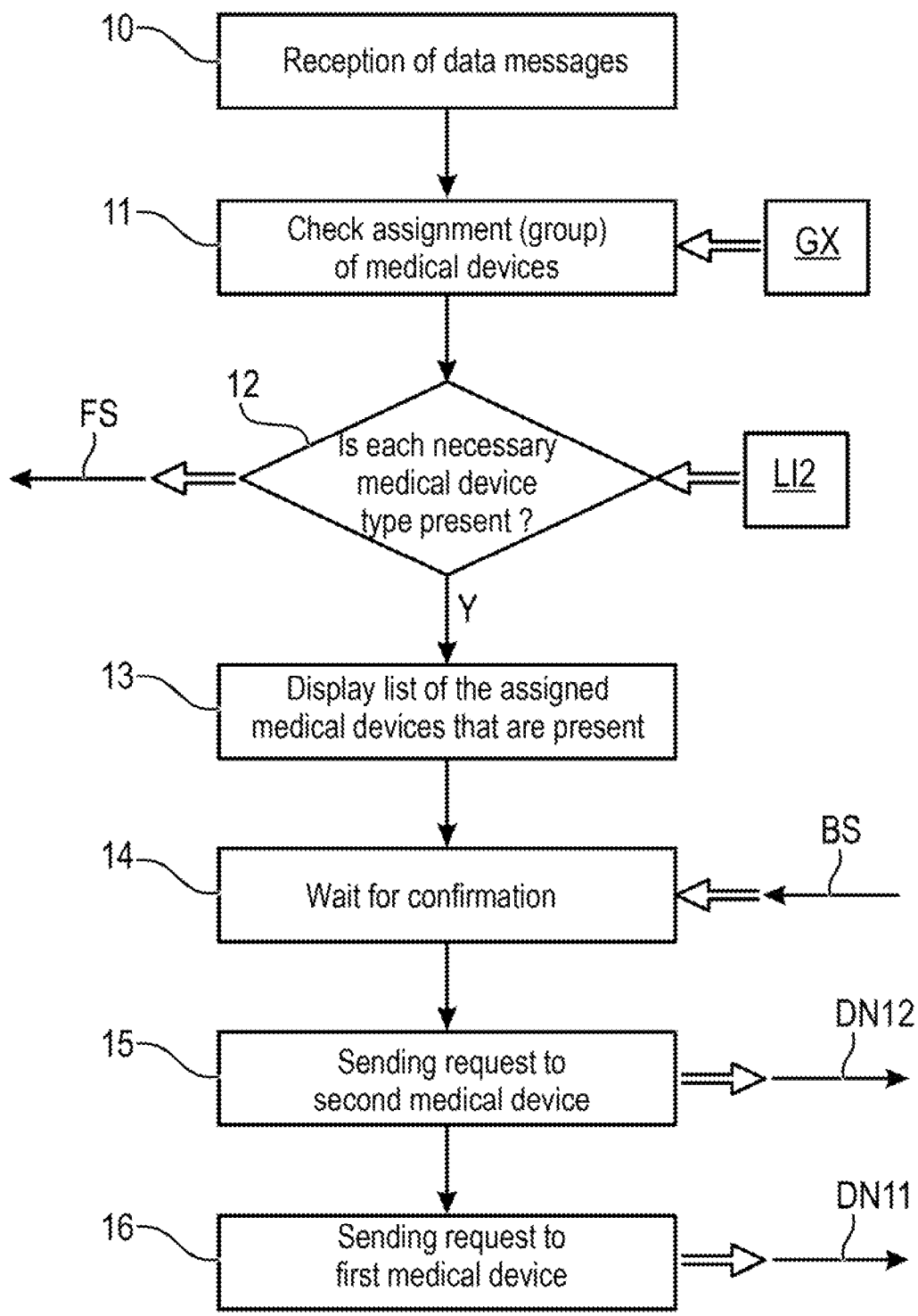
FIG. 3 is a flow chart showing steps that can be carried out according to a preferred embodiment by the control unit of the device according to the present invention.

FIG. 3 shows preferred steps, which can be carried out on the control unit S of the device V from FIG. 1.

In a step 10, data messages are received, which were sent by medical devices, for example, the medical device MG1 or MG2 according to FIG. 1.

Figure 2A:
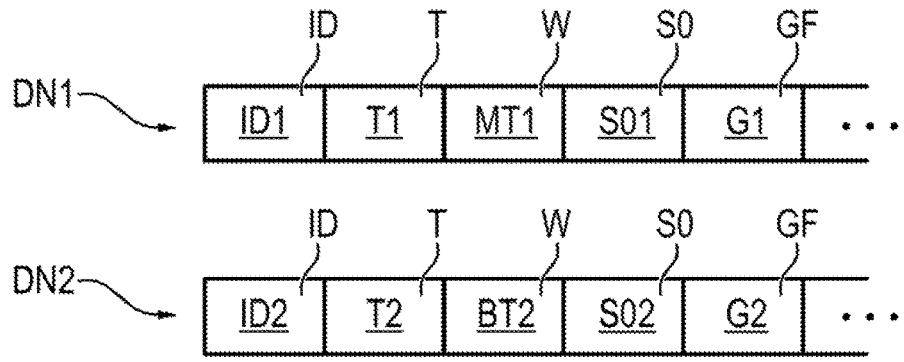
FIG. 2a is a schematic view showing different request messages.

FIG. 2a shows exemplary data messages DN1, DN2.

The data message DN1 contains in an identification field ID identification data ID1, which indicate, for example, a network identity or medical device identity of the medical device MG1 from FIG. 1.

The data message DN1 further has a type field T, in which a data element T1 indicates the medical device type of the medical device MG1 according to FIG. 1.

A medical device type may be, for example, a ventilator, an anesthesia device, a patient monitor, an EMG measuring device, a blood pressure-measuring device, a syringe pump or another type of medical device.

In a value field W, a data element MT1 indicates measured values, which can be provided by the medical device, which has sent the message DN1.

In a location field SO, a data element SO1 indicates a location of the medical device in question. The location may be a room number, a ward number or another type of location information, for example, a corresponding hospital bed.

In a group field GF, a group data set G1 indicates a group affiliation of the medical device in question.

FIG. 2a further shows data message DN2, which can be sent by the medical device MG2 according to FIG. 1.

The data message DN2 contains data fields, which correspond to the data fields of the data message DN1, with the exception that the data field W contains a data element BT2, which indicates at least one operating parameter, which can be changed or selected on the medical device in question as a function of an information signal, which can be received via the data network interface in the form of a data signal during its data message.

Figure 2B:
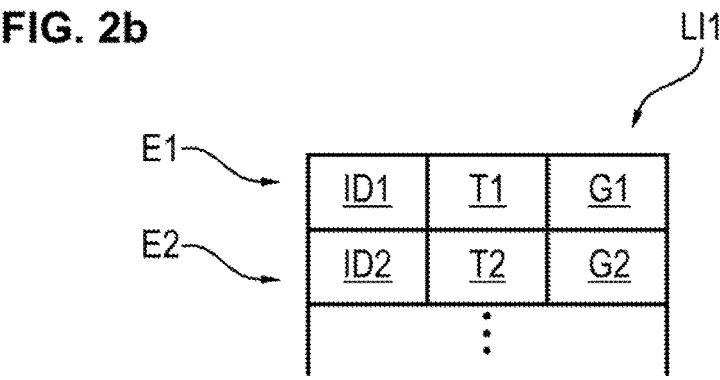
FIG. 2b is a schematic view showing a data set for tracking information from received data messages.

FIG. 2b shows a data set or a list LI1, in which the medical devices found and identified on the basis of the data messages DN1, DN2 are detected and tracked.

The respective data elements G1, G2 for indicating the respective group affiliation may have identical values, so that a joint current assignment to the same common group may consequently be given.

Figure 2C:
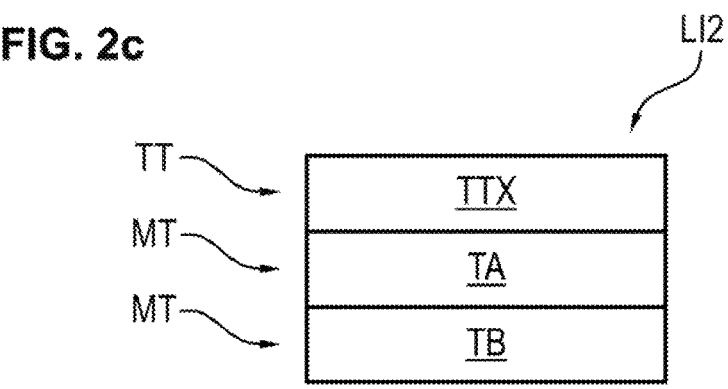
FIG. 2c is a schematic view showing a medical device data set in a preferred embodiment.
Figure 2D:
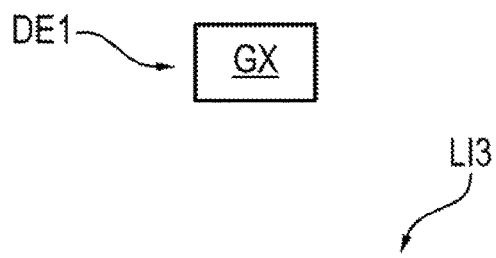
FIG. 2d is a schematic view showing a data element, which indicates a predefined group.

FIG. 2d shows a data set DE1 with a data element GX, which was preferably loaded in advance into the memory unit SP of the device V. The memory unit SP consequently provides a data element GX or a data set DE1, which indicates a predefined group of medical devices or predefined group identity of medical devices. The data element GX may have been configured by the user in advance by an input on the device V by means of the input unit E. As an alternative or in addition, data element GX may be selected by the control unit S in advance and stored correspondingly for selecting the predefined group or group identity on the basis of data messages DN received at the device via the data interface DS.

By comparing the group identities G1, G2 from the data set well as the group identity indicated by the data element GX, the control unit S of the device then consequently can determine a current joint assignment of the first medical device MG1 and of the second medical device MG2 to a common, predefined group in the data network.

The memory unit SP of the device V preferably provides a medical device data set LI2 from FIG. 2c. The medical device data set LI2 indicates a certain combined therapy type in a therapy type field TT by means of a data element TTX as well as a set of necessary medical device types corresponding to the combined therapy type in medical device fields MT by means of corresponding type data elements TA, TB.

FIG. 3 further shows a step 11, in which an assignment of previously found or identified medical devices to a predefined group is checked. The control unit S uses for this the data element GX or the corresponding data set DE1 from FIG. 2d in order to check the assignment of medical devices to the corresponding predefined group.

Figure 2E:
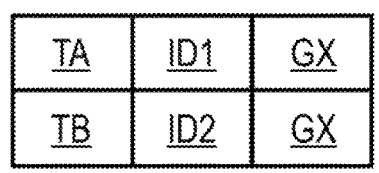
FIG. 2e is a schematic view showing a data set, which indicates currently jointly assigned medical devices.

FIG. 2e shows a list or a data set LI3, in which the detected current joint assignment of the medical devices MG1, MG2 from FIG. 1 to the corresponding group, which is indicated by the data element GX, is recorded or tracked.

According to FIG. 3, the medical device data set LI2 provided by the memory unit SP is used in a step 12 to check whether a corresponding medical device is currently assigned to the common group for each of the necessary medical device types TA, TB. The data set LI3 from FIG. 2e may preferably be used for this as well.

In case a corresponding medical device is currently assigned to the group for each necessary medical device type from the corresponding set of medical device types TA, TB for the combined therapy type TTX, a control signal is preferably cleared by the control unit S of the device V for clearing the input unit for a potential input of a confirmation signal. This control signal for clearing is shown as a signal FS in FIG. 3.

Consequently, if it was determined in step 12 that the first medical device MG1 and the second medical device MG2 with their respective identities ID1, ID2 are assigned to the common, predefined group GX, a list of these medical devices, which are present and are assigned to the group, is then displayed in a step 13.

It is checked in a next step 14 whether a confirmation signal BS is received from the input unit E at the control unit S. If the confirmation signal BS is present, the control unit S sends a request message DN12 to the second medical device MG2 via the data network interface DS.

Figure 4A:
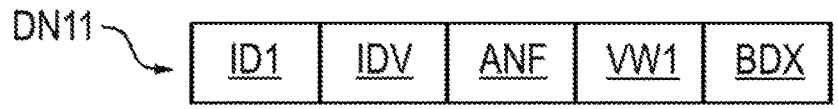
FIG. 4a is a schematic view showing a preferred embodiment of a request message.
Figure 4B:
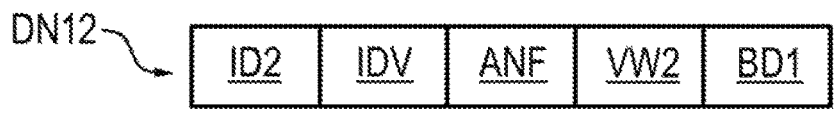
FIG. 4b is a schematic view showing another preferred embodiment of a request message.

A preferred embodiment of the request message DN12 is shown in FIG. 4b.

The request message DN12 preferably indicates a network identity ID2 of the second medical device MG2 as well as a network identity IDV of the device V, which sends the message DN12. The request message DN12 further has a data element ANF, which indicates a request that the medical device MG2 receiving the message DN12 activate the operating state of the combined therapy. Consequently, the data element DNF is thus a data element that indicates a request that the medical device MG2 that is to receive the message DN12 shall select at least one operating parameter of its actuator AK as a function of an information signal from the first medical device MG1, which information signal is received via the data network.

In a next step 16, the control unit S sends via the data network interface DS a data message DN11, which is an additional request message. This request message DN11 is shown in FIG. 4a.

By means of a data element ANF, the data message DN12 indicates as a request message a request that the medical device MG1 that is to receive the data message DN11 activate the operating state of the combined therapy in the first medical device MG1. The request message DN11 consequently indicates a request ANF to detect physiological measured values by means of the sensor signal SI and to generate an information signal on the basis of the physiological measured values as well as to provide the information signal in the form of a data message to the medical device MG2 via the data network.

Figure 5:
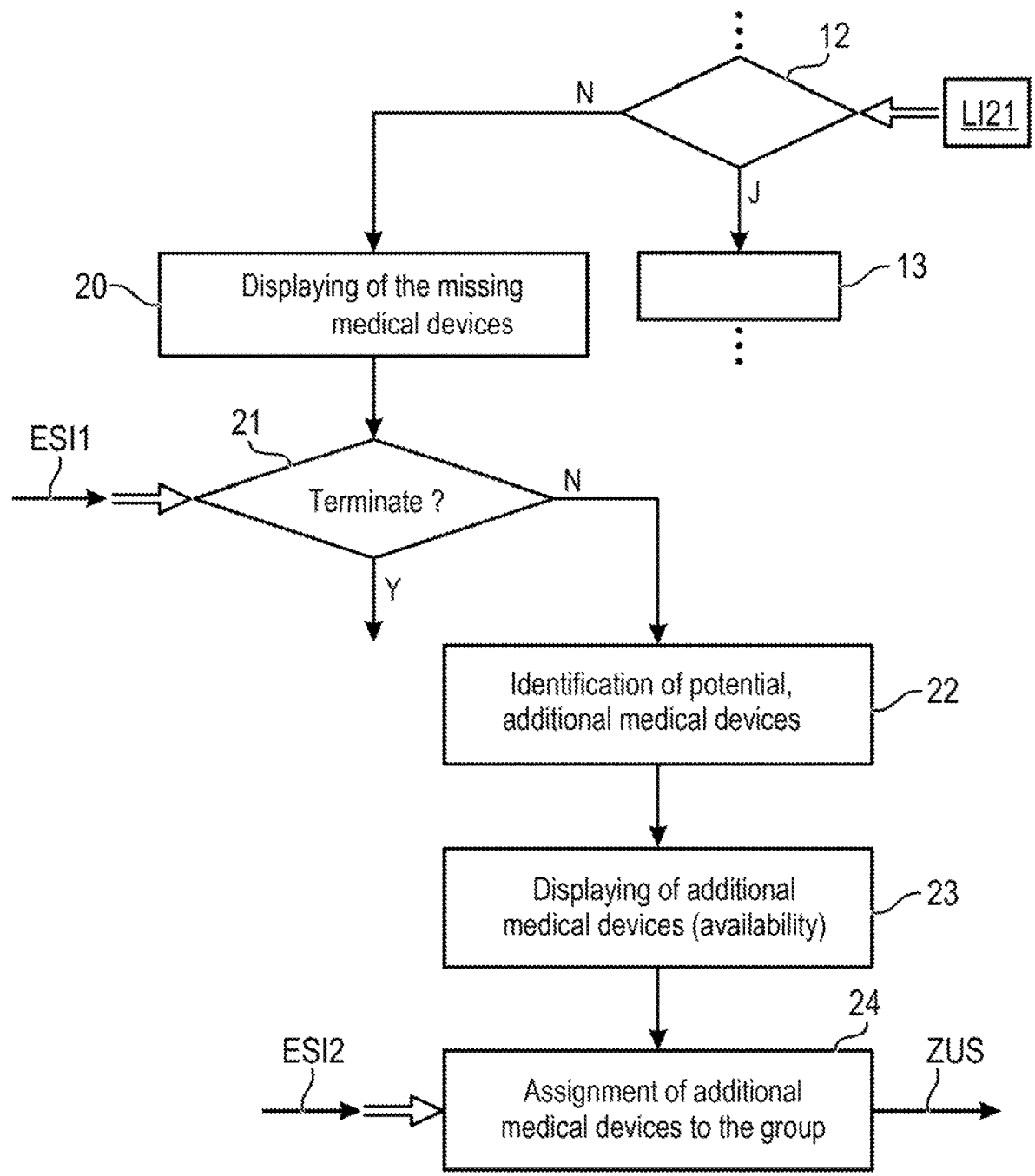
FIG. 5 is a flow chart showing steps of a preferred partial method, which can be carried out on the control unit of the device.

FIG. 5 shows preferred steps, which can be carried out on the control unit S of the device V.

FIG. 5 shows at first the step 12, which was already explained with reference to FIG. 3. It is possible here that an alternative medical device data set LI21 from FIG. 4d can be used instead of the medical device data set LI2 from FIG. 2c.

The medical device data set LI21 indicates a corresponding set of three medical device types TA, TB, TC for the combined therapy type TTX.

The process now returns to FIG. 5. If it is determined in step 12 that a corresponding medical device is currently assigned to the common group for each necessary medical device type, the process is branched off further, as was already described above with reference to FIG. 3, to the method step 13.

In case no corresponding medical device is assigned to the common group for at least one of the indicated medical device types, here, for example, to the medical device type TC, the process is branched off to a step 20.

The medical device type from the corresponding set to which no corresponding medical device is currently assigned to the common, predefined group, is then displayed to the user in step 20.

As was mentioned above, this may be effected in the form of a list with individual entries related to the necessary medical device types.

Then, if a corresponding input signal ESI1 is predefined, the configuration of the medical devices of the data network is terminated in a step 21. Consequently, if the input signal ESI1 indicates the wish of a user to terminate this configuration, no further steps are carried out, which is indicated by an arrow branching off to the left in FIG. 5.

One or more additional medical devices, which are present in the data network and are potentially considered for the combined therapy type TTX based on their corresponding medical device type, are then identified in a step 23 on the basis of received data messages as well as of the medical device data set LI21. This can be achieved by means of the control unit by identifying a medical device, which is present in the data network and has the corresponding medical device type TC, by a comparison of the medical device type TC, for which no corresponding medical device is currently assigned as yet to the common group.

Figure 4C:
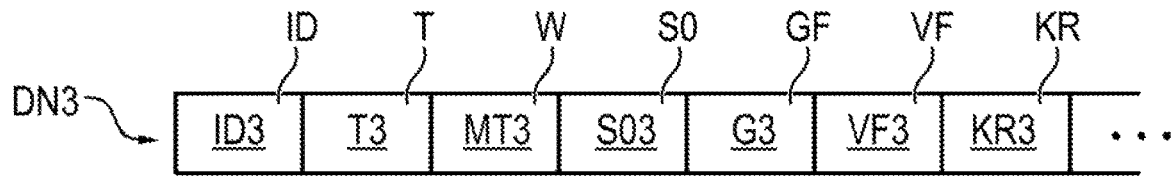
FIG. 4c is a schematic view showing a preferred embodiment of a data message.
Figure 4D:
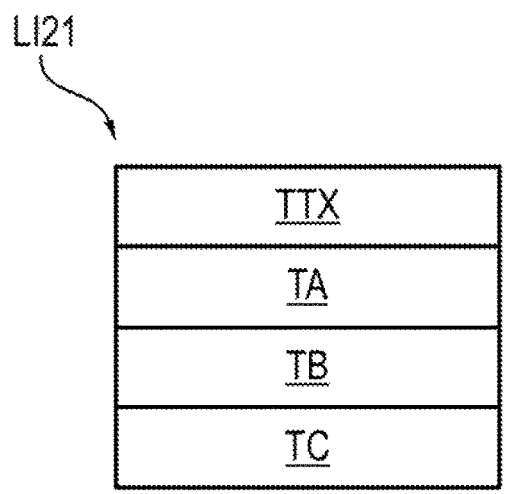
FIG. 4d is a schematic view showing a medical device data set in a preferred embodiment.

For example, such a medical device can be identified for this, for example, on the basis of a data message D3 from FIG. 4c.

If the medical device type T3 of the corresponding medical device agrees with the medical device type TC from the medical device data set, but the group affiliation, indicated by the data set G3 of the message DN3, is such that the corresponding medical device is not yet assigned to the current predefined group GX, the control unit can then select the corresponding medical device with the identification or with the identity data ID3, as another medical device that may potentially be considered and then display it to the user in step 23 of FIG. 5.

The data message DN3 of FIG. 4c preferably contains an availability field VF, in which a corresponding data element VF3 indicates an availability of the corresponding medical device.

Such an availability is then displayed together with the identity of the medical device in step 23 from FIG. 5.

An availability may be information related to a physical location of the medical device.

As an alternative, the availability may be information related to a distance of the corresponding medical device from the device V receiving the message DN3.

As an alternative, the availability may be information related to a switched-on status of the medical device. This may consequently be information that the device is switched on, switched off or is in a standby mode.

The displaying of the one additional medical device or of the additional medical devices in step 23 may preferably take place in an order that depends on a predefined criterion.

The data message DN3 of FIG. 4c may preferably have for this in a criterion field KR a data element KR3, which indicates a criterion value.

A criterion may be, for example, a required quality of physiological measured values, which is to be complied with by a medical device.

As an alternative, a criterion may be a parameter for a quality level of a medical device.

Another possibility for a criterion may be a distance of the corresponding medical device from the location of the device V shown in FIG. 1.

Another criterion may be a distance of the corresponding medical device from a location of a patient, who is likewise assigned to the common, predefined group of medical devices.

In another step 24, the additional medical device, for example, the one with the identity ID3 from FIG. 4c, can then be assigned to the current common and predefined group GX as a function of an input signal ESI2, which is received at the control unit S via the input unit E. This may be carried out, for example, by the data set LI3 of FIG. 2e being expanded by an entry, in which the identity ID3 of the additional medical device is stored together with the group identity GX for the medical device type TC. The assignment of the additional medical device to the common predefined group may preferably also be carried out by an assignment signal ZUS being sent, in the form of a data message, to the additional medical device in question, i.e., to the one with the identity ID3.

Such a data message or assignment message then contains a data element, which indicates as the recipient the corresponding additional medical device, i.e., the one with the identity ID3, as well as the corresponding group or group affiliation GX via a data element.

FIG. 6b shows steps that are preferably to be carried out and which preferably precede step 10 from FIG. 3.

A medical device data set LI22, which indicates respective, corresponding sets of a plurality of necessary medical device types for respective combined therapy types, is provided in a step 31.

This medical device data set LI22 is shown in detail in FIG. 6.

Respective necessary medical device types are indicated for respective combined therapy types TTX, TTY, TTZ in different entries E11, E12, E13. For example, a set of medical device types that comprises a medical device type TA and a medical device type TB is necessary for the therapy type TTX.

According to FIG. 6b, the combined therapy types indicated in the medical device data set L122 is then displayed in step 31.

A selection of a certain combined therapy type is determined in a step 32 via an input signal EIS3 of a user, which signal is provided at the control unit S via the input unit E.

It consequently becomes possible as a result that the respective, corresponding set of the plurality of necessary medical device types is also selected for the selected combined therapy type in an automated manner by a simple selection of a certain combined therapy type with the use or on the basis of the medical device data set LI22.

FIG. 6c shows steps that are preferably carried out prior to step 10 of FIG. 3 but also preferably still before step 31 of FIG. 6b.

The selection of a certain user is determined in a step 41 as a function of an input signal EIS of the input unit E.

The user is a clinician, who will then later configure the corresponding medical devices MG1, MG2 of FIG. 1 for the combined therapy by means of the device V.

An identification data set LI5, which indicates one or more identities of respective authorized users, is provided in step 42. It can be stated in an alternative manner that the identification data set LI5 indicates any respective identity data sets for respective authorized users.

Figure 8A:
FIG. 8a is a schematic view showing a data set, which indicates predefined values for operating parameters of an actuator of a medical device.
Figure 8B:
FIG. 8b is a schematic view showing a data set, which indicates data for user identification.

FIG. 8b shows for this the data set LI5, in which corresponding identity or identification data UID1 are stored for a user U1.

Such an identification data set IUD1 may be a password, a string of symbols, a PIN code, a combination of numbers, a fingerprint, an iris scan or another form of an identification data set. The identification data set is preferably a combination of one or more types of the above-mentioned types of identification data sets.

An input signal EIS5 is then received in step 42 via the input unit E or another input unit, wherein the additional input unit may be, for example, an iris scanner, a device for fingerprint recognition, a keyboard or another form of an input unit.

An authorization or identity of the user is then checked in step 42 on the basis of the identification data set SLI5 as well as of the input signal EIS5.

The control unit S according to FIG. 1 then makes the possibility of inputs into the input unit E for generating the confirmation signal BS, likewise shown in FIG. 1, for configuring the medical device MG1, MG2 via the device V and dependent upon a comparison of the identification data set LI5 or of a part of same and the input signal EIS5.

If the result of the identification check is positive, the input unit E is unblocked in a step 43.

If the result of the identity or authorization check is negative, the input unit is blocked in step 44.

The control unit S preferably unblocks the input unit E in step 43 for generating the confirmation signal BS for a predefined duration.

The predefined duration begins from the time of adjustment of the positive comparison result or identification result from step 42. The predefined time is a predefined time window with a predefined duration, which can be predefined by a data element from the memory unit SP.

It is known from FIG. 4b as well as from FIG. 4a and the corresponding description below that corresponding request messages DN12 and DN11 can be sent to the medical devices MG2 and MG1, respectively, from the device V. Such a request message DN12 may then preferably indicate a predefined value by a data element VW2, which is a predefined value relative to at least one operating parameter of the actuator of the medical device MG2.

This predefined value is, for example, a predefined pressure value, to which an actuator in the form of a gas feed unit of a ventilator can be regulated.

FIG. 8a shows a data set LI4, which indicates a desired predefined value by means of a data element VW2 for a combined therapy type TTX and for a certain medical device type TB. An additional predefined value in the form of an additional data element VW21 may preferably also be indicated for this medical device type TB.

It is further possible that the list LI4 or this data set for additional combined therapy types indicates additional corresponding predefined values related to additional medical device types.

The control unit S now consequently receives the corresponding predefined value or the corresponding data element VW2 from the data set LI4 of FIG. 8a and includes these in the request message DN12.

The control unit S may analogously include a predefined value in the form of a data element VW1 in the data message DN1 for the first medical device MG1 from a data set not explicitly shown here. The predefined value indicated by the data element VW1 may then be, for example, a parameter, which can be used by the control unit S1 to obtain the physiological measured values from the sent signal SI.

FIG. 6a further shows in the medical device data set LI22 at least one predefined condition for a combined therapy type TTX in the form of the data element BD1, which condition must be met during the course of the combined therapy of this therapy type. This predefined condition in the form of the data element BD1 may then be included in the request message DN12 of FIG. 4b, so that the control unit S indicates this predefined condition in the initial message DN12. The inclusion of the condition or of the corresponding data element BD12 in the request message DN12 is thus a request to the medical device MG2 receiving the message DN12 to monitor the corresponding condition during the operating state of the combined therapy for this corresponding therapy type.

Such a condition may preferably be a threshold value for a physiological measured value, which must not be exceeded and/or undershot.

As an alternative, such a condition may be a threshold value for a value of an operating parameter of the actuator AK, which must not be exceeded or undershot.

As an alternative, such a condition may be a state of activity or a switched-on state of the medical device MG2 or of a component of the medical device MG2.

As an alternative, such a condition may be a minimum required quality of physiological measured value measured values, and this may pertain especially and preferably to physiological measured value measured values that are indicated in the information signal IS by the first medical device MG1.

Such a condition may preferably be a maximum latency period of a data transmission between the two medical devices MG1, MG2. Such a latency period may be measured, for example, on the basis of the control units S1, S2 by implementing corresponding data network protocols.

Such a condition may preferably be a location, preferably a room, in which the medical device MG2 in question is located, which shall not be changed during the operating state of the combined therapy.

Such a condition may preferably be a group affiliation, for example, an affiliation to the group GX, which must not be changed during the operating state of the combined therapy for the medical device MG2.

Figure 7A:
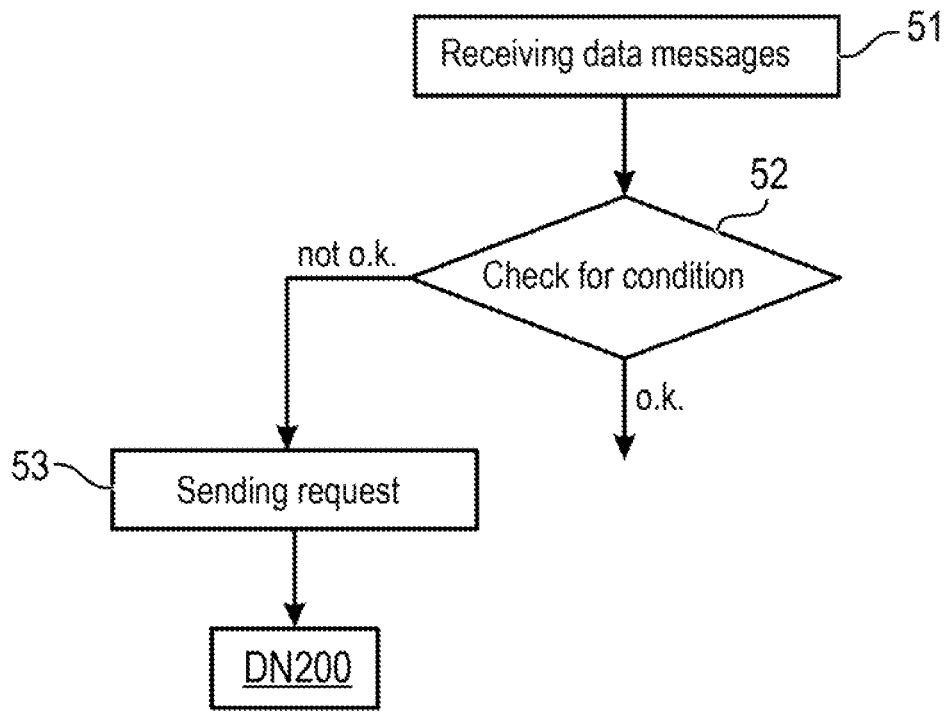
FIG. 7a is a flow chart showing steps of a partial method, which can be carried out on the control unit.

FIG. 7a shows steps that the control unit S of the device V can carry out after sending the request messages DN12, DN11 during steps 15, 16 of FIG. 3. The medical devices MG1, MG2 are in the operating state of combined therapy in this case.

Figure 7B:
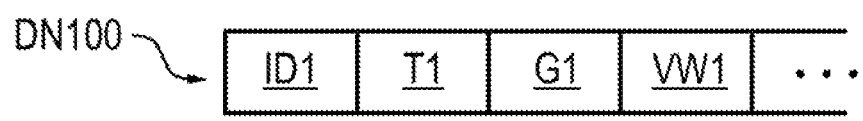
FIG. 7b is a schematic view showing a preferred embodiment of a data message.

In step 51, the control unit S receives data messages from involved medical devices MG1, MG2, such a data message preferably being a data message DN100 from FIG. 7b.

The data message DN100 preferably has a data element VW1, which indicates a violation of the condition indicated above. On the basis of the received data message DN100, the control unit S then checks in step 52 whether the condition indicated or required before, which corresponds to the data element BD1 of the data message DN12 or to the data element BDX of the data message DN1 of FIG. 4a, is violated.

If the condition is violated, i.e., if the result of the checking is negative, the process is branched off to a step 53, in which a request message DN200 is sent to the first and/or second medical device MG1, MG2.

Figure 7C:
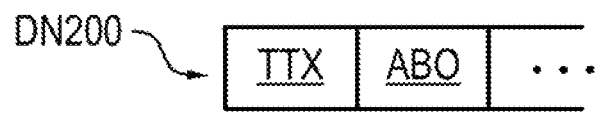
FIG. 7c is a schematic view showing a preferred embodiment of a request message.

The data message DN200 is shown in FIG. 7c. The data message DN200 as a request message indicates a request to terminate the operating state of the combined therapy; this preferably takes place by including a corresponding data element ABO in the data message DN200 in FIG. 7c.

Consequently, a checking of the required conditions can thus be carried out by the device V itself and it does not therefore have to be performed by a corresponding medical device MG2 alone.

Returning to FIG. 1, the medical device MG2, which has an actuator AK for physiologically directly or indirectly influencing the patient PA, is considered once again.

Figure 10A:
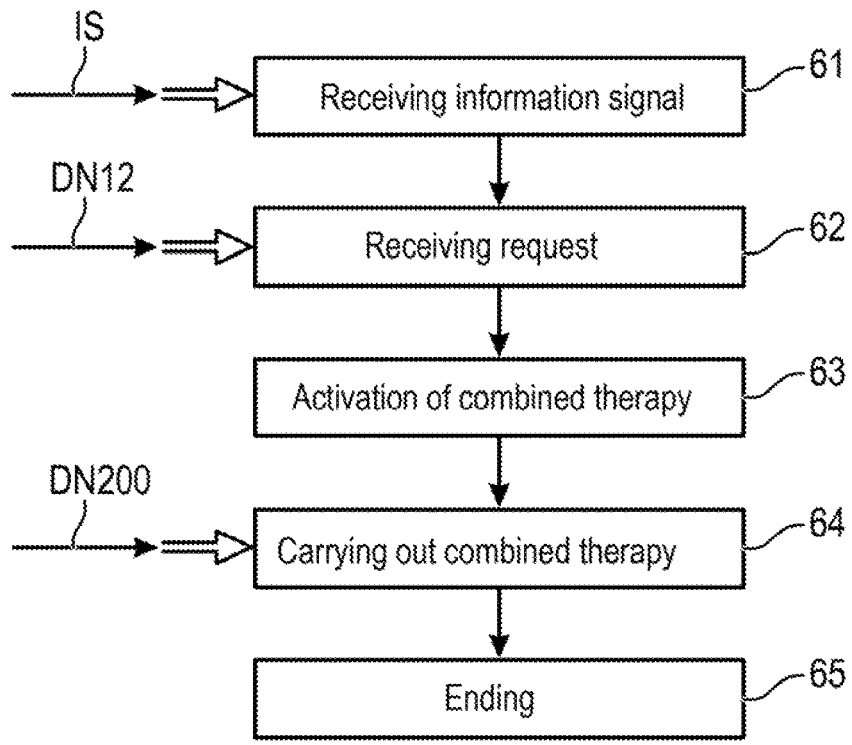
FIG. 10a is a flow chart showing steps of a preferred method, which can be carried out on the control unit of the medical device according to the present invention.

The control unit S2 can preferably carry out steps of the method from FIG. 10a.

In a step 61, the medical device MG2 already receives with its control unit the information signal IS of the first medical device MG1 from FIG. 1.

This information signal IS does not absolutely have to be used here to actuate the actuator AK, so that the operating state of the combined therapy may not possibly be present in the medical device MG2 as yet.

Upon receipt of the request message DN12, the operating state of the combined therapy is activated in the medical device MG2 in step 62. Consequently, at least one operating parameter of the actuator AK is then selected by the control unit S in this operating state of the combined therapy as a function of the information signal IS received.

The activation of the combined therapy takes place in step 63.

The combined therapy is then carried out in step 64.

Upon receipt of the request message DN200, the control device then ends the operating state of the combined therapy and changes over to step 65.

Figure 10B:
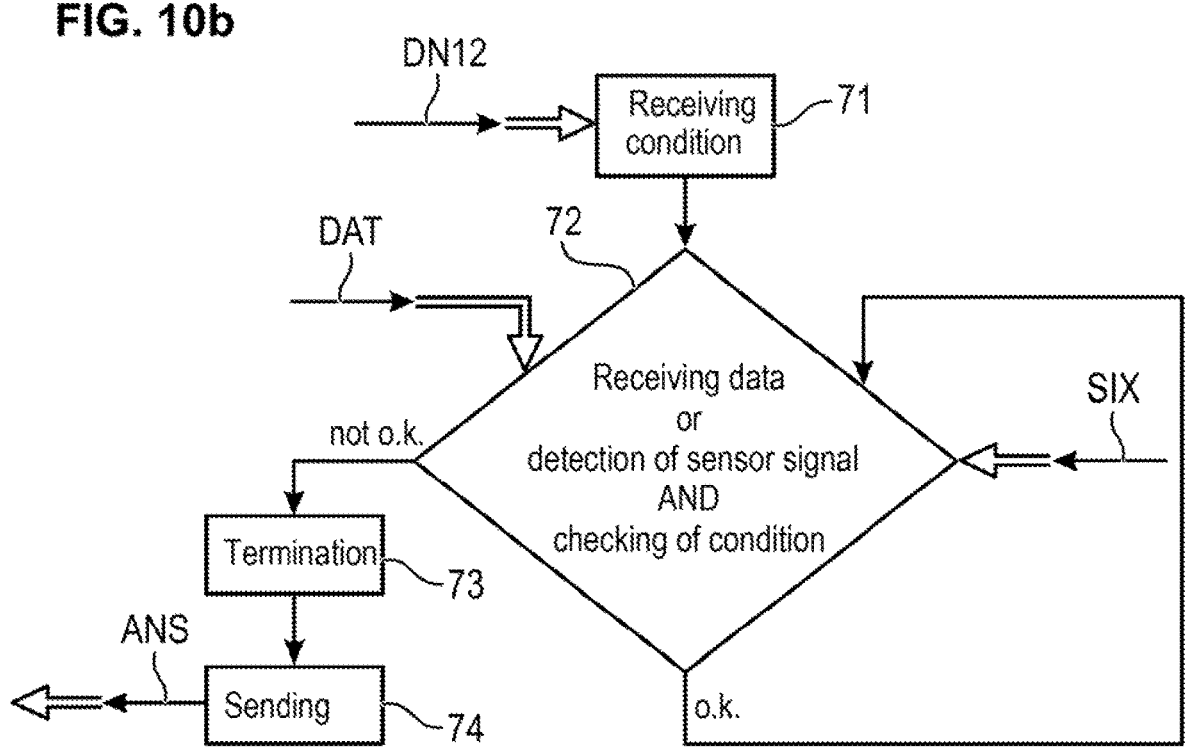
FIG. 10b is a flow chart showing steps of a preferred partial method, which can be carried out on the control unit of the medical device.

FIG. 10b shows steps that can be carried out on the control unit S2 of the medical device MG2.

The above-mentioned predefined condition, which is to be checked and must be met during the operating state of the combined therapy, is predefined or indicated in a step 71 on the basis of the data message DN12.

Based on data messages DAT received via the data interface DS2 and/or the own sensor signal, the control unit S2 then checks in a step 72 whether the predefined condition is met.

If the condition is met, the control unit S remains in step 72.

If the condition is not met, the control unit S branches off to a step 63, in which the operating state of the combined therapy is terminated or ended.

A request message or a request signal ANS is then sent in a step 74 to at least one other network device of the data network, for example, of the device V and/or of the medical device MG1, wherein this initial message—request message—ANS indicates a request for ending the combined therapy.

Figure 8C:
FIG. 8c is a schematic view showing a preferred form of a request message or of a request signal.

FIG. 8c shows for this such an exemplary initial message—request message—ANS, which contains, in addition to a recipient identity IDZ, a data element ABO, which indicates a request for ending the operating state of the combined therapy.

As an alternative, the data element ABO indicates information that the operating state was ended in the medical device MG2 in question.

Figure 9A:
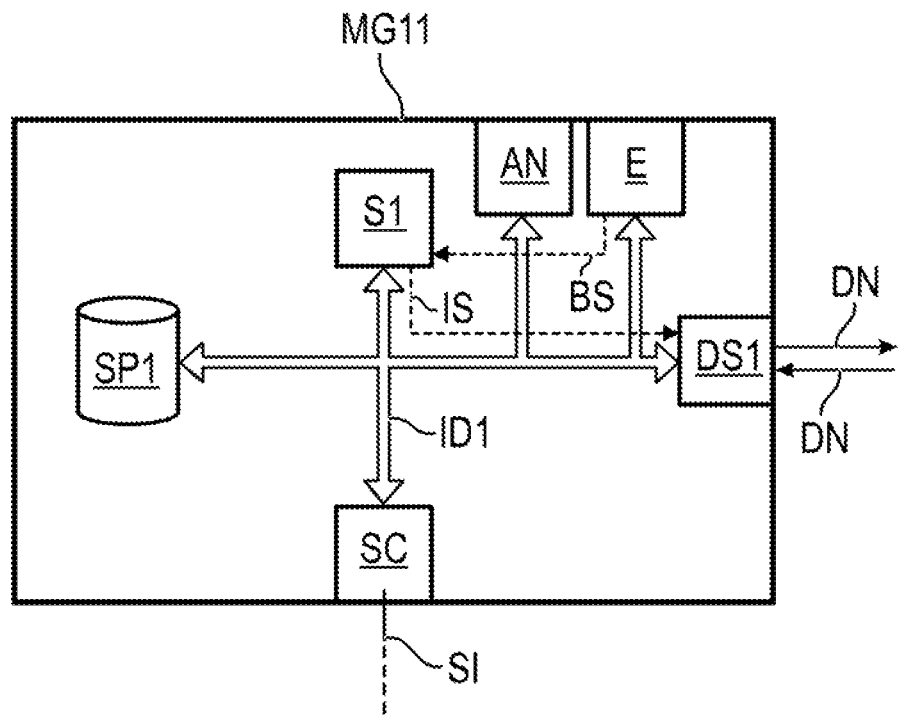
FIG. 9a is a schematic view showing a preferred embodiment of a medical device.
Figure 9B:
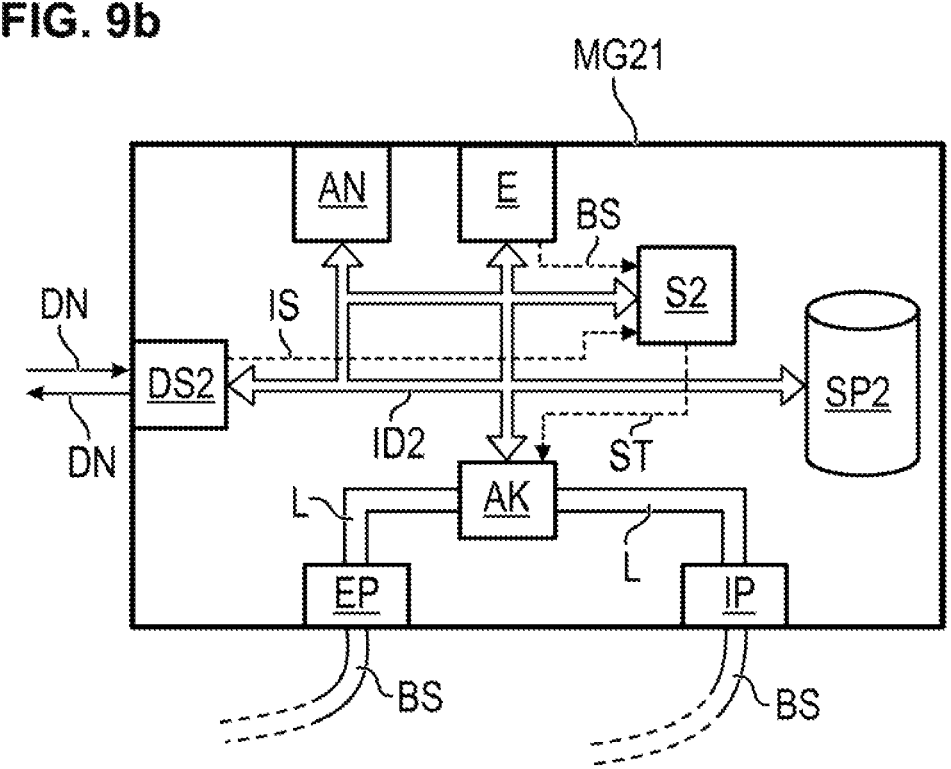
FIG. 9b is a schematic view showing another preferred embodiment of a medical device.

FIGS. 9a and 9b show modified medical devices MG11, MG21, which additionally have the display unit AN as well as the input unit E of the device V, unlike the medical device MG1 or MG2 according to FIG. 1.

The corresponding control units S1, S2 may be configured here such that the above-described functionalities of the control unit S of the device V from FIG. 1 can be carried out by one of the control units S1 or S2 of the medical devices MG11 or MG21.

It can therefore be seen that even though the device according to the present invention for controlling operating states of medical devices in a medical data network may be a separate, central data network device, like the device V from FIG. 1, all these functionalities of the device V can nevertheless also be implemented just as well in one of the medical devices MG11 or MG12.

The memory units SP1 and SP2 are configured now corresponding to the memory unit SP of the device V.

Even though some aspects were described in connection with a device, it is obvious that these aspects also represent a description of the corresponding method, so that a block or a component of a device may also be defined as a corresponding method step or as a feature of a method step. Analogously hereto, aspects that were described in connection with a method step or as a method step also represent a description of a corresponding block or detail or feature of a corresponding device.

Depending on certain implementation requirements, exemplary embodiments of the present invention may be implemented in hardware and/or in software. In particular, a control unit may be implemented in hardware and/or in software. The implementation may be carried out with the use of a digital storage medium, for example, a floppy disk, a DVD, a Blu-Ray disk, a CD, a ROM, a PROM, an EPROM, an EEPROM or a FLASH memory, a hard drive or another magnetic or optical memory, on which electronically readable control signals are stored, which control signals can or do interact with a programmable hardware component such that the method in question is carried out.

A programmable hardware component may be formed by a processor, a computer processor (CPU=Central Processing Unit), a graphics processor (GPU=Graphics Processing Unit), a computer, a computer system, an application-specific integrated circuit (ASIC=Application-Specific Integrated Circuit), an integrated circuit (IC=Integrated Circuit), a one-chip system (SOC=System on Chip), a programmable logic element or a field-programmable gate array with a microprocessor (FPGA=Field Programmable Gate Array).

The digital storage medium may therefore be machine- or computer-readable. Some exemplary embodiments consequently comprise a data storage medium, which has electronically readable control signals, which are capable of interacting with a programmable computer system or with a programmable hardware component such that one of the methods described here is executed. An exemplary embodiment is consequently a data storage medium (or a digital storage medium or a computer-readable medium), on which the program for executing the method described here is recorded.

Exemplary embodiments of the present invention may generally be implemented as program, firmware, computer program or computer program product with a program code or as data, wherein the program code acts or the data act in such as way as to execute one of the methods when the program is running on a processor or on a programmable hardware component. The program code or the data may also be stored, for example, on a machine-readable medium or data storage medium. The program code or the data may be present, among other things, as source code, machine code or byte code as well as other intermediate code.

Another exemplary embodiment is, furthermore, a data stream, a signal sequence or a sequence of signals, which represent the program for executing one of the methods described here. The data stream, the signal sequence or the sequence of signals may be configured, for example, such as to be transferred via a data communication connection, for example, via the internet or another network. Exemplary embodiments are thus also signal sequences representing data, which are suitable for transmission vie a network or a data communication connection, wherein the data present the program.

A program according to one exemplary embodiment may implement one of the methods during its execution, for example, by reading storage locations or writing a datum or a plurality of data into these, as a result of which switching operations or other procedures are brought about in transistor structures, in amplifier structures or in other electrical, optical, magnetic components or components operating according to another principle of operation. Data, values, sensor values or other information may correspondingly be detected, determined or measured by a program by reading a storage location. A program may therefore detect, determine or measure variables, values, measured variables and other information by reading one or more storage locations as well as bring about, prompt or execute an action by writing to one or more storage locations as well as actuate other devices, machines and components.

While specific embodiments of the invention have been shown and described in detail to illustrate the application of the principles of the invention, it will be understood that the invention may be embodied otherwise without departing from such principles.

What is claimed is:

1. A state controlling device for controlling an operating state of at least one medical device for a combined therapy of a patient by the interaction of at least two medical devices in a medical data network, wherein a first medical device is configured to detect physiological measured values of a patient in an operating state of a combined therapy, further to generate an information signal on the basis of the physiological measured values as well as to provide the information signal via the data network, and wherein a second medical device has an actuator for physiologically influencing the patient and is further configured to select at least one operating parameter of the actuator as a function of the information signal of the first medical device, which is received via the data network, in the operating state of the combined therapy, wherein the state controlling device comprises:

a state controlling device structure for controlling the operating state of at least one medical device, the state controlling device structure comprising:
a data network interface;
an input unit for inputs of a user;
an optical display unit for outputting information to the user; and
a control unit configured:
to determine a current joint assignment of the first medical device and of the second medical device to a common group in the data network on the basis of data messages received via the data network interface;

to display to the user the current joint assignment of the first and second medical devices to the group via the display unit in case of a positive result of the determination; and upon receipt of a confirmation signal from the input unit, to send a request message to the second medical device, which indicates a request to activate the operating state of the combined therapy in the second medical device, wherein the combined therapy is configured to be carried out via at least the first medical device and the second medical device.

2. A state controlling device in accordance with claim 1, wherein:

the request message is a first request message; and the control unit is further configured to send a second request message, which indicates a request to activate the operating state of the combined therapy in the first medical device, to the first medical device in the presence of the confirmation signal.

3. A state controlling device in accordance with claim 1, further comprising a memory unit configured to provide a medical device data set, which indicates for a combined therapy type a corresponding set of medical device types necessary for the combined therapy type, wherein the control unit is further configured:

to determine on the basis of the data set and of the data messages received whether a corresponding medical device of the common group is currently assigned for each indicated medical device type from the set; and in case no corresponding medical device is currently assigned to the common group for at least one of the indicated medical device types, to display to the user via the optical display unit the particular necessary, indicated medical device types to which no corresponding medical device is currently assigned in the common group.

4. A state controlling device in accordance with claim 3, wherein the control unit is further configured to prevent the sending of the request message as a function of an input signal of the input unit.

5. A state controlling device in accordance with claim 3, wherein the control unit is further configured:

to identify at least one additional medical device from the data network, which is potentially considered for the combined therapy type, on the basis of the medical device data set and the data messages received; and to display the at least one additional medical device to the user via the optical display unit.

6. A state controlling device in accordance with claim 5, wherein the control unit is further configured:

to determine information related to an availability of the at least one additional medical device on the basis of the data messages received; and to display the information to the user via the display unit.

7. A state controlling device in accordance with claim 5, wherein the control unit is further configured to perform an assignment of the at least one additional medical device to the common group as a function of an input signal.

8. A state controlling device in accordance with claim 3, wherein the control unit is configured:

to identify a plurality of additional medical devices from the data network, which are not yet assigned to the common group but are potentially considered for the combined therapy type on the basis of the data messages received; and to display via the display unit the plurality of additional medical devices in an order that depends on a predefined criterion.

9. A state controlling device in accordance with claim 3, wherein:

the medical device data set further indicates for at least one combined therapy type at least one predefined condition, which must be met during the course of a combined therapy type; and the control unit is configured to indicate the predefined condition in the request message.

10. A state controlling device in accordance with claim 9, wherein the control unit is configured:

to check whether the predefined condition is met on the basis of data messages received via the data interface; and if the result of the checking is negative, to send at least one request message to the first medical device or to the second medical device or to both the first medical device and the second medical device, wherein the at least one request message indicates a request to terminate the operating state of the combined therapy.

11. A state controlling device in accordance with claim 1, wherein:

the medical device data set indicates respective, corresponding sets of a plurality of necessary medical device types for respective combined therapy types; and the control unit is configured:

to display the respective combined therapy types to the user via the display unit; and to determine a selection of a certain combined therapy type as a function of an input of the user via the input unit.

12. A state controlling device in accordance with claim 1, further comprising a memory unit configured to provide an identification data set, which indicates one or more identities of respective authorized users, wherein the control unit is configured:

to receive an input signal, which indicates an identity of the user, via the input unit or another input unit; and to control the input unit such that the control unit makes a possibility of input into the input unit for generating the confirmation signal dependent on a comparison of the identification data set and the input signal, which indicates the identity of the user.

13. A state controlling device in accordance with claim 12, wherein the control unit is configured to make possible an input, for generating the confirmation signal in case of a positive result of the comparison, for a predefined duration only.

14. A state controlling device in accordance with claim 1, wherein the request message indicates at least one predefined value relative to at least one operating parameter of the actuator.

15. A system in accordance with claim 1, wherein the state controlling device further comprises a memory unit configured to provide a medical device data set, which indicates for a combined therapy type a corresponding set of medical device types necessary for the combined therapy type, wherein the control unit is further configured:

to determine on the basis of the data set and of the data messages received whether a corresponding medical device of the common group is currently assigned for each indicated medical device type from the set; and in case no corresponding medical device is currently assigned to the common group for at least one of the indicated medical device types, to display to the user via the optical display unit the particular necessary, indicated medical device types to which no corresponding medical device is currently assigned in the common group.

16. A medical device for a medical data network, the medical device comprising:
a medical device structure comprising:
an actuator for physiologically influencing a patient;
a data network interface; and
a control unit configured to control the actuator and the control unit is configured:
to select an operating parameter of the actuator as a function of at least one information signal received via the data network interface from another medical device; and
to activate an operating state of a combined therapy in the medical device upon receipt of a request message, wherein the combined therapy is carried out via the medical device and the another medical device.

17. A medical device in accordance with claim 16, wherein the control unit is further configured to end the operating state of the combined therapy in the medical device upon receipt of another request message.

18. A medical device in accordance with claim 16, wherein the control unit is further configured:
to receive via the data network interface a request message, which indicates at least one predefined condition, which must be met during the operating state of the combined therapy;
to check whether the predefined condition is met on the basis of data messages received via the data interface or to check whether the predefined condition is met on the basis of medical device sensor signals from sensors of the medical device or to check whether the predefined condition is met on the basis of data messages received via the data interface and on the basis of medical device sensor signals from sensors of the medical device; and
to end the operating state of the combined therapy if the result of the checking is negative.

19. A medical device in accordance with claim 16, wherein:
the control unit is further configured to send, if the result of the checking is negative, at least one request message to at least one other network device of the data network; said at least one request message indicates a request to end the combined therapy.

20. A system, comprising:
a first medical device;
a second medical device;
a medical data network;
a state controlling device for controlling an operating state of at least one of the first medical device and the second medical device for a combined therapy of a patient by the interaction of at least the first medical device and the second medical device in the medical data network, wherein the first medical device is configured to detect physiological measured values of a patient in an operating state of a combined therapy, further to generate an information signal based on the physiological measured values as well as to provide the information signal via the data network, and wherein the second medical device has an actuator for physiologically influencing the patient and the second medical device is further configured to select at least one operating parameter of the actuator as a function of the information signal of the first medical device, which is received via the data network, in the operating state of the combined therapy, wherein the state controlling device comprises:
a data network interface;
an input unit for inputs of a user;
an optical display unit for outputting information to the user; and
a control unit configured:
to determine a current joint assignment of the first medical device and of the second medical device to a common group in the data network on the basis of data messages received via the data network interface;
to display to the user the current joint assignment of the first and second medical devices to the group via the display unit in case of a positive result of the determination; and
upon receipt of a confirmation signal from the input unit, to send a request message to the second medical device, which indicates a request to activate the operating state of the combined therapy in the second medical device such that the combined therapy is carried out via the first medical device and the second medical device.

* * * * *

UNITED STATES PATENT AND TRADEMARK OFFICE
CERTIFICATE OF CORRECTION

| | | |
|---|---|---|
| PATENT NO. | : 11,529,052 B2 | Page 1 of 1 |
| APPLICATION NO. | : 15/850559 | |
| DATED | : December 20, 2022 | |
| INVENTOR(S) | : Kullik et al. | |

It is certified that error appears in the above-identified patent and that said Letters Patent is hereby corrected as shown below:

On the Title Page

Item (30) Foreign Application Priority Data please add:
Dec. 22, 2016 (DE) .................... 10 2016 015 685.6

Signed and Sealed this
Twenty-first Day of February, 2023

Katherine Kelly Vidal
*Director of the United States Patent and Trademark Office*